United States Patent

DeGroot et al.

[11] Patent Number: 5,986,149
[45] Date of Patent: Nov. 16, 1999

[54] METHOD FOR RECOVERING ALKANOLS FROM AQUEOUS HBR-SOLUTIONS

[75] Inventors: Richard J. DeGroot, West Lafayette, Ind.; James T. Ayers, ElDorado, Ark.; Karl E. Reineke, Lafayette, Ind.

[73] Assignee: Great Lakes Chemical Corporation, West Lafayette, Ind.

[21] Appl. No.: 09/054,640

[22] Filed: Apr. 3, 1998

Related U.S. Application Data

[60] Provisional application No. 60/043,903, Apr. 3, 1997.

[51] Int. Cl.⁶ .......................... C07C 27/10; C07C 37/68
[52] U.S. Cl. .......................... 568/700; 568/724; 568/725; 568/726
[58] Field of Search .................... 568/700, 724, 568/725, 726

[56] References Cited

U.S. PATENT DOCUMENTS

| | | | |
|---|---|---|---|
| 1,253,055 | 1/1918 | Lacy | 568/700 |
| 1,688,726 | 10/1928 | McKee | 568/700 |
| 4,013,728 | 3/1977 | Brackenridge | 260/619 A |
| 4,990,321 | 2/1991 | Sato et al. | 423/486 |
| 5,059,722 | 10/1991 | Mitchell et al. | 568/726 |
| 5,138,110 | 8/1992 | Segall et al. | 570/258 |
| 5,145,612 | 9/1992 | Reay et al. | 568/700 |
| 5,395,994 | 3/1995 | Williams et al. | 568/913 |
| 5,446,212 | 8/1995 | Sanders et al. | 568/726 |
| 5,685,169 | 11/1997 | Nagamura et al. | 62/617 |
| 5,723,690 | 3/1998 | McKinnie | 568/726 |
| 5,847,232 | 12/1998 | McKinnie | 568/726 |

FOREIGN PATENT DOCUMENTS

9843717  10/1998  WIPO .

*Primary Examiner*—Louise N. Leary
*Attorney, Agent, or Firm*—Woodard, Emhardt, Naughton, Moriarty & McNett

[57] ABSTRACT

The present invention provides processes for recovering alkanols from fluids comprising the alkanol and aqueous hydrobromic acid without forming excessive amounts of alkyl bromide. In certain aspects of the invention, there are provided distillation systems wherein a fluid comprising an alkanol and aqueous hydrobromic acid is introduced into a distillation column at a point between the bottom and the top of the column to thereby separate the alkanol and the hydrobromic acid without causing the production of a significant amount of alkyl bromide. A process for separating an alkanol from aqueous hydrobromic acid which comprises (a) refluxing aqueous HBr in a fractionating column (10) having a port (15) located between the top (19) and bottom (11) ends of the column and in fluid communication with the column; (b) feeding into the column through the port a first fluid comprising an alkanol and aqueous HBr; (c) recovering from the top end of the column a second fluid comprising at least 50% of the alkanol; and (d) recovering at the bottom end of the column a third fluid comprising at least 50% of the aqueous HBr.

30 Claims, 3 Drawing Sheets

METHOD FOR RECOVERING ALKANOLS FROM AQUEOUS HBR-SOLUTIONS

REFERENCE TO RELATED APPLICATION

The present application claims priority upon U.S. Provisional patent application Ser. No. 60/043,903, filed Apr. 3, 1997, which is hereby incorporated by reference herein in its entirety.

BACKGROUND OF THE INVENTION

1. Field of the Invention

The present invention relates generally to processes for the recovery of alkanols from fluids comprising the alkanol, hydrobromic acid and water, without the formation of excessive amounts of alkyl bromide. More specifically, the invention relates to a distillation system wherein a fluid comprising an alkanol, hydrobromic acid and water is introduced into a distillation column at a point between the bottom and the top of the column to thereby separate the alkanol and the hydrobromic acid without causing the production of a significant amount of alkyl bromide.

2. Discussion of Related Art

It is known that lower alkyl bromides can be readily prepared from the reaction of hydrobromic acid with the corresponding alkanol. For example, U.S. Pat. No. 5,138,110 to Segall describes a process for the continuous production of lower alkyl halides from hydrogen halide and an alkanol in an aqueous acid solution. Indeed, when the acid is hydrobromic acid ("HBr"), and the temperature is elevated, it is difficult to prevent the reaction from occurring; however, lower temperatures and the presence of large amount of water are factors known to retard alkyl bromide formation. The water serves both to dilute the reactants and to drive the following reaction back to the alkanol:

Certain operations in the chemical industry result in process streams comprising an aqueous solution of alkanol and HBr, and it is typically necessary to separate the components for recycle. The separation can be accomplished by simple distillation, but a large percentage of the components are lost to the formation of alkyl bromide during the procedure. The alkyl bromide formation occurs both in the distillation flask because of the relatively long residence time at elevated temperature, and probably also in the vapor phase until such time as the components are separated by rectification. In a process wherein the alkanol is methanol, large quantities of volatile methyl bromide can be produced. At one time this was advantageous because the methyl bromide could be advantageously sold as a valuable soil fumigant; however, methyl bromide has recently been classified as an ozone depleting chemical, and its production is becoming highly restricted. Due to the severe impact on production costs which would result if the methyl bromide is collected only to be destroyed by incineration, there is a great need for the development of processes which avoid or minimize alkyl bromide production.

An example of a process well known in the industry which produces streams of aqueous alkanol mixed with HBr, is the manufacture of tetrabromobisphenol-A ("TBBPA"), which is widely used as a flame retardant for synthetic resins. Typically, bisphenol-A is dissolved in an alkanol or aqueous alkanol (generally methanol, ethanol or propanol), and elemental bromine is added thereto and reacted to form TBBPA. One mole of hydrogen bromide is generated for each bromine atom that is inserted onto the aromatic rings. As the bisphenol-A is brominated, it becomes less soluble and begins to drop out of solution. Additional water is commonly added to further promote precipitation. The product is isolated by filtration and further treated to improve purity. For example, it may be washed with water or a water/alkanol solution, and the wash (now comprising HBr and alkanol) may be optionally added to the mother liquor for recycle. While alkanol solvents are the most useful and most economical solvents for use in TBBPA processes, a serious disadvantage of employing an alkanol solvent in a TBBPA process is that at least a portion of the generated HBr reacts with the alkanol to form alkyl bromide during bromination or during subsequent alkanol/HBr separation.

In the TBBPA process, options do exist for minimization of undesirable alkyl bromide formation, both during bromination, and during solvent recovery. With respect to the former, for example, it is well known that mixing water with the alkanol solvent retards alkyl bromide formation to a certain degree; however, high levels of water also reduce solubility and can cause underbrominated species to precipitate with the product, lowering assay. Further, the alkanol must still be separated from the HBr, and separation techniques known in the art cause additional alkyl bromide to be produced.

Other approaches to minimizing alkyl bromide formation during bromination involve avoiding the use of alkanols completely, or removing HBr from the bromination system as it is generated. For example, in U.S. Pat. No. 4,013,728 to Brackenridge it is disclosed that TBBPA may be brominated in aqueous acetic acid rather than in methanol or other alkanol. This approach is not totally satisfactory, however, because it is often difficult to dry the last traces of acetic acid from the precipitate, resulting in an undesirable odor in the product. Further, alkanols are excellent solvents for the TBBPA process, being economical and having many of the necessary solvating properties to provide high quality product. Alternatively, U.S. Pat. No. 5,446,212 to Sanders et al. discloses that alkyl bromide formation may be reduced by removing HBr from the bromination system as it is generated via addition of an oxidizing agent, such as hydrogen peroxide, into the bromination system. Addition of the oxidizing agent results in conversion of HBr to elemental bromine:

This approach is not completely satisfactory, however, because it is impractical to convert all of the HBr to bromine. Therefore, while this approach minimizes the amount of HBr in a mother liquor, it does not eliminate its presence therein.

As stated above, another processing step which results in the generation of alkyl bromides is the separation step performed after bromination to recover the alkanol solvent. There have been a number of processes described in the prior art for minimizing alkyl bromide production in the separation step. For example, U.S. Pat. No. 5,395,994 to Williams et al. discloses the neutralization of HBr prior to recovering the alkanol solvent, and German Patent DE 3341037 to Jenkner et al. discloses that the HBr in an ethanol-based mother liquor from the production of hexabromocyclododecane can be neutralized with an alkanolamine prior to distillation. While this may be an effective approach, it requires the use of large amounts of base and the addition of extra water. It is a significant disadvantage of this approach that the base and the water must be disposed of or treated for reuse.

U.S. Pat. No. 4,990,321 to Sato et al. discloses a method for addressing the problem by diluting the solution to less than 10% HBr by weight before distillation. This does reduce alkyl bromide formation, but, again, introduces a significant amount of water to the system which must be removed and disposed of or treated for reuse. Accordingly, there remains a need for a simple, economical process for separating lower boiling alkanols from aqueous solutions of HBr without excessive alkyl bromide formation.

SUMMARY OF THE INVENTION

It has now been discovered that lower boiling alkanols can be advantageously recovered from aqueous HBr using a simple distillation process. Fundamental to the process is short residence time at elevated temperature, which is accomplished by the continuous introduction of the solution directly into a fractionating column as opposed to feeding it into a distillation vessel itself. Conditions are selected such that the alkanol and some of the water quickly disengage from the solution and are carried overhead, while the acid, the remaining water and any solids are condensed and flow into the reboiler. Quick separation within the column greatly reduces the amount of alkyl bromide formed. The feed to the fractionating column may be in liquid form, or as a vapor of the liquid which has been flash distilled. The invention is particularly useful in the production of tetrabromobisphenol-A, wherein the mother liquor typically comprises, in addition to other materials, an alkanol and aqueous HBr, and wherein the generation of alkyl bromides is preferably kept to a minimum.

The present invention in one aspect provides a process for separating an alkanol from aqueous hydrobromic acid, comprising (1) providing a reflux environment of aqueous hydrobromic acid in a fractionating column having a bottom end, a top end, and a port located between the top and bottom ends and in fluid communication with the column; (2) feeding into the column through the port a first fluid comprising an alkanol and aqueous hydrobromic acid; (3) recovering from the top end a second fluid comprising at least about 50% of the alkanol; and (4) recovering from the bottom end a third fluid comprising at least about 50% of the aqueous hydrobromic acid.

The present invention also provides a process for separating an alkanol from aqueous hydrobromic acid, comprising (1) providing a distillation system comprising a distillation column having a bottom end, a top end and a port located between the top and bottom ends in fluid communication with the column; first means adjacent the bottom end and in fluid communication with the column for receiving a bottoms product from the column; and second means adjacent the top end and in fluid communication with the column for receiving a distillate; wherein a fourth fluid is contained in the first means; and wherein the fourth fluid is a liquid; (2) boiling the fourth fluid to provide a reflux environment in the column; (3) feeding into the column through the port a first fluid comprising an alkanol and aqueous hydrobromic acid; (4) recovering from the second means a second fluid comprising at least about 50% of the alkanol; and (5) recovering from the first means a third fluid comprising at least about 50% of the aqueous hydrobromic acid.

In another aspect of the invention, there is provided a process for separating an alkanol from aqueous hydrobromic acid, comprising (1) providing a distillation system comprising a distillation column having a bottom end, a top end and a port located between the top and bottom ends in fluid communication with the column; a vessel attached to the column adjacent the bottom end and in fluid communication with the column; and a condenser attached to the column adjacent the top end and in fluid communication with the column; wherein a fourth fluid is contained in the vessel; and wherein the fourth fluid is a liquid; (2) boiling the fourth fluid to provide a reflux environment in the column; (3) feeding into the column through the port a first fluid comprising an alkanol and aqueous hydrobromic acid; (4) recovering from the condenser a second fluid comprising at least about 50% of the alkanol; and (5) recovering from the vessel a third fluid comprising at least about 50% of the aqueous hydrobromic acid.

It is an object of the invention to provide a process for separating lower boiling alkanols from aqueous HBr in a simple, cost effective system, without generating a significant amount of corresponding alkyl bromides.

It is another object of the invention to provide a process for separating alkanol from a mother liquor produced in the manufacture of TBBPA.

It is also an object of the invention to provide a process for manufacturing TBBPA, using an alkanol as the bromination solvent, wherein the alkanol is recovered from the mother liquor without the formation of significant amounts of alkyl bromide.

Further objects, advantages and features of the present invention will be apparent from the detailed description herein.

BRIEF DESCRIPTION OF THE FIGURES

Although the characteristic features of this invention will be particularly pointed out in the claims, the invention itself, and the manner in which it may be made and used, may be better understood by referring to the following description taken in connection with the accompanying figures forming a part hereof.

DETAILED DESCRIPTION OF PREFERRED EMBODIMENTS

For purposes of promoting an understanding of the principles of the invention, reference will now be made to particular embodiments of the invention and specific language will be used to describe the same. It will nevertheless be understood that no limitation of the scope of the invention is thereby intended, such alterations and further modifications in the invention, and such further applications of the principles of the invention as described herein being contemplated as would normally occur to one skilled in the art to which the invention pertains.

Figure 1:
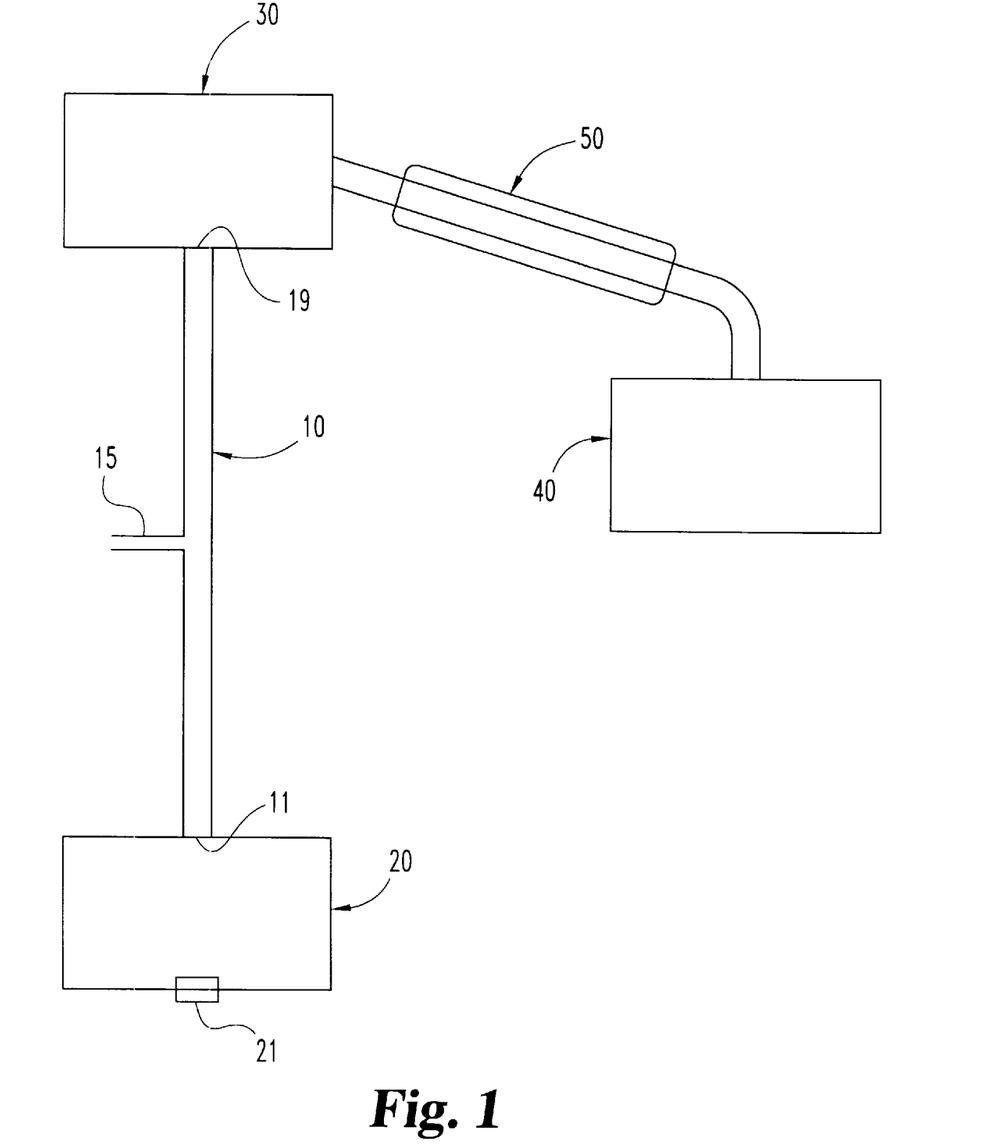
FIG. 1 is a schematic diagram of an inventive distillation system.

Provided by the invention are processes for separating an alkanol from aqueous hydrobromic acid by distilling a fluid comprising both components, preferably in a continuous manner. Fundamental to the process is that the fluid must reside at an elevated temperature in the column only for a short time before separation occurs. Significant difficulties have been encountered in the prior art of separating an alkanol from HBr because, when the mixture is heated, the alkanol reacts with HBr to yield the corresponding alkyl bromide. Separation is achieved in accordance with the invention by continuously introducing the fluid into a fractionating column 10 for rapid separation rather than into a reboiler 20. Conditions are selected in the column such that the alkanol and some of the water quickly disengage from the fluid and are carried overhead, while the hydrobromic acid, the remaining water, and any non-volatile materials in the mixture are condensed and flow into a vessel 20 fluidly connected to the bottom of the column 10 (i.e., a reboiler). While it is not intended that the present invention be limited by any theory whereby it achieves its advantageous result, it is believed that excellent separation is achieved without the problematic formation of alkyl bromide because the separation within the column occurs so rapidly.

A starting material needed to practice the invention, therefore, is a fluid comprising an alkanol and aqueous hydrobromic acid. The present invention may advantageously be practiced, of course, using fluids that also comprises additional compositions, such as, for example, alkyl bromide and non-volatile materials. When alkyl bromide is present, it will also be separated from the hydrobromic acid ("HBr"), and will come to reside in the head product along with the alkanol. Separation of the alkanol and the alkyl bromide may then be advantageously achieved using processes well known in the art. While higher alkyl bromide concentrations are acceptable, it is preferred that the feed comprise no greater than about 40% alkyl bromide. When non-volatile materials are present in the feed, such materials advantageously pass to the reboiler 20, where they may advantageously be drained through an outlet 21 in the bottom of the reboiler 20.

The alkanol in a fluid to be separated in accordance with the invention preferably has a boiling point of less than about 120° C. Preferred alkanols are those the have from about 1 to about 4 carbon atoms, including linear and branched chain alkanols such as, for example, methanol, ethanol, n-propanol, isopropanol, isomers of butanol, pentanol and mixtures thereof. While fluids comprising a wide variety of proportions of alkanol may be advantageously separated in accordance with the invention, a fluid will preferably comprise at least about 5% alkanol by weight so that separation thereof will be economically worthwhile. More preferably, the fluid feed comprises from about 20% to about 80% alkanol by weight and, most preferably, from about 40% to about 60%.

The aqueous hydrobromic acid in a fluid to be separated in accordance with the invention may comprise a wide variety of proportions of water and HBr. It is preferred that the ratio of HBr to water in the fluid be from about 20:80 to about 45:55 by weight. Higher ratios of HBr will result in the formation of a 48% HBr azeotrope in the column, leading to an unsatisfactory increase in the amount of alkyl bromide formed in the column. While ratios lower than about 20:80 are acceptable in an inventive separation system, a fluid featuring a lower ratio comprises sufficient water that it can be separated using a normal pot feed distillation system, such as that depicted in FIG. 3, without forming an excessive amount of alkyl bromide. It is preferred that the fluid feed comprise from about 5% to about 47% HBr by weight, more preferably from about 15% to about 30% HBr by weight.

In a preferred aspect of the invention, the fluid comprises a weight ratio of alkanol to hydrobromic acid of from about 10:90 to about 98:2, more preferably from about 35:65 to about 85:15 and, most preferably, from about 65:35 to about 75:25. Tetrabromobisphenol-A ("TBBPA") mother liquor is a fluid by-product of large-scale industrial processes which may be advantageously separated in accordance with the invention. As used herein, the term "TBBPA mother liquor" is intended to refer to an aqueous alkanol/HBr stream that is produced in the manufacture of TBBPA. It is common for a TBBPA mother liquor to also include non-volatile materials such as, for example, brominated phenols. Under conditions of an inventive process, the non-volatile materials in a TBBPA mother liquor will come to reside in the vessel 20, and will advantageously form a separate phase in the vessel 20 which may be drained or pumped from the vessel 20 to permit the separation process to be advantageously run in a continuous fashion.

Separation of an alkanol and an aqueous hydrobromic acid is advantageously achieved in accordance with the invention using an apparatus having a distillation column 10 with a feed port 15 positioned between the bottom 11 and the top 19 of the column 10. The port 15 advantageously provides a conduit for feeding the fluid into the column 10. Preferably, the port 15 is positioned a distance of from about one tenth to about nine tenths of the length of the column from the bottom 11 of the column 10. Thus, for example, if a column is used that is ten meter long, the port 15 is preferably positioned from about 1 meter to about 9 meters from the bottom of the column. More preferably, the port 15 is positioned from about one fifth to about four fifths of the column length from the bottom 11 and, most preferably, from about one half to about two thirds of the column length from the bottom 11.

The apparatus also comprises a vessel 20 attached adjacent the bottom 11 of the column 10 and in fluid communication with the column, and a condenser 50 attached in fluid communication with the top 19 of the column 10. While it is expected that a wide variety of distillation columns will separate the fluid into an upper alkanol-rich phase and a lower acid-rich phase, it is preferred that the column contain solid structures therein. Examples of such structures are packing materials and plates. For example, an Oldershaw column or a packed column is advantageously used in accordance with particular preferred aspects of the invention.

Figure 2:
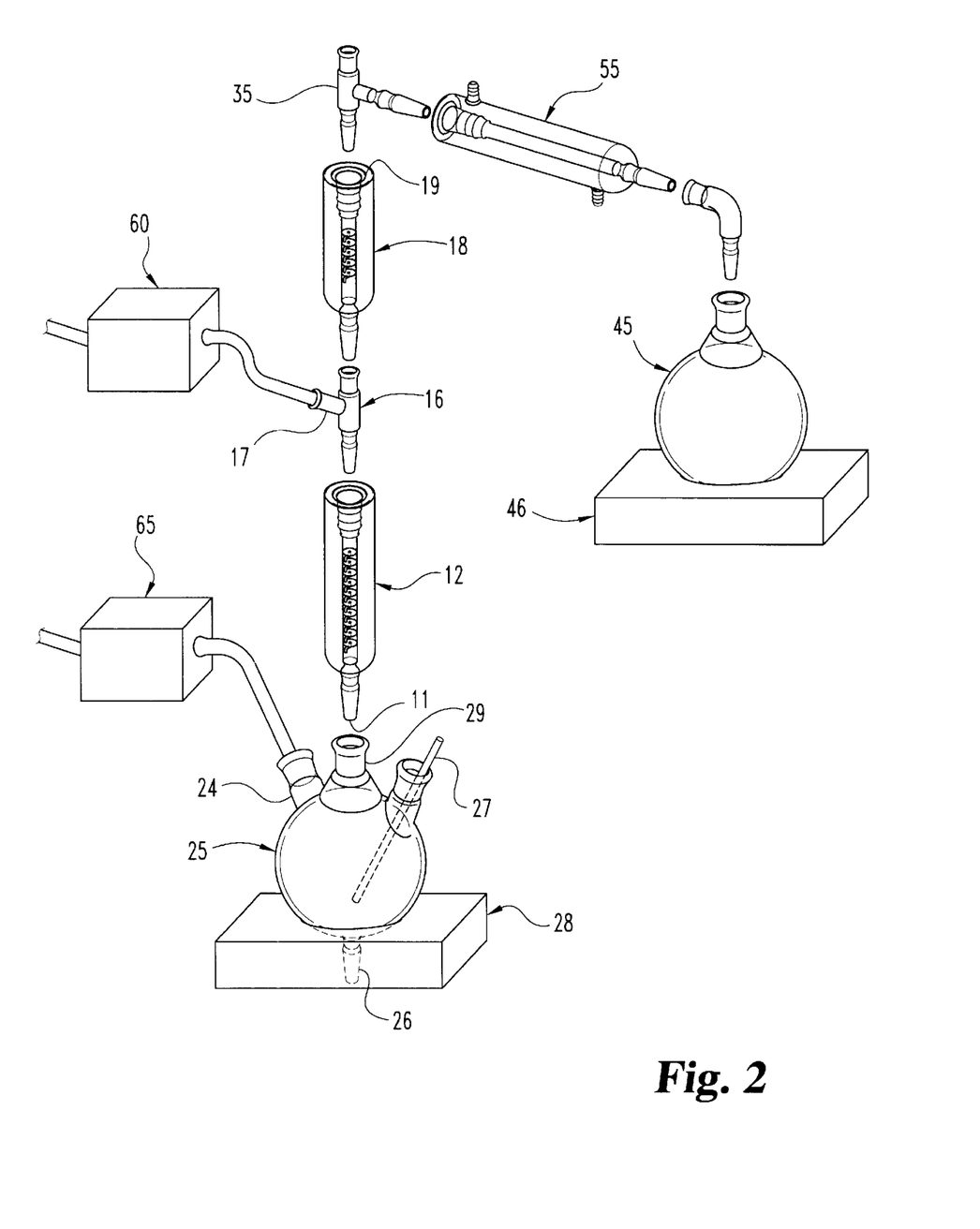
FIG. 2 illustrates a preferred laboratory-scale embodiment of the present invention.

In a preferred manner of practicing the invention, using a system such as that depicted in FIG. 2, two Oldershaw columns 12, 18 are connected using a Claisen adapter 16 having a side arm 17. The side arm 17 therefore comprises the port and the two columns 12, 18 and the adapter 16 combine to form a continuous column having a port between the bottom 11 and the top 19 of the column. The height of the column, the number of theoretical plates and the location of the feed port are variables which may be selected, without undue experimentation, by a person skilled in the art, depending upon the identity of the alkanol being separated and the concentrations of components in the fluid. In a preferred aspect of the invention, the Oldershaw column comprises about ten stripping trays and about five rectification trays. Also, a distillation head 30 is typically positioned between, and in fluid communication with, the column 10 and the condenser 50. The distillation head 30 may be selected which advantageously provides excellent control of distillate composition, such as, for example, a magnetically controlled distillation head. Alternatively, a conventional distillation head 35 may be used. The system also preferably comprises a receptacle 40 for receiving the distillate from the condenser 50. It is readily understood that a wide variety of alternate configurations may be used in a system having the features described and claimed herein, and that highly preferred apparatus may be designed on an industrial scale for separating a large stream of feed fluid. Such variations are expressly included within the scope of the invention.

The distillation may be carried out at atmospheric pressure, under moderate positive pressure or in a vacuum. It may be run in batch, semi-continuous or continuous fashion, but a continuous process is preferred. The feed to the fractionating column may be in liquid form, or as a vapor of the liquid which has been vaporized using methods which expose the liquid to elevated temperatures for short periods of time. These methods include, for example, thin film, falling film or wiped film techniques. Based upon the description herein, one skilled in the art will be able to select designs and operating conditions which optimize the recovery of the alkanol and minimize alkyl bromide formation.

In a preferred manner of performing a separation in accordance with the invention, a vessel 20 is provided in fluid communication with a distillation column 10 as described. Into the vessel 20 is charged a start-up reflux fluid to advantageously prepare the column for the influx of feed fluid, the start-up reflux fluid preferably comprising aqueous HBr, more preferably less than 48% HBr by weight, and most preferably from about 20% to about 45% HBr by weight. This start-up reflux fluid is heated until vapors reflux into the column. It is readily understood that the column may be prepared as described by refluxing a wide variety of fluids into the column. While it is preferred in certain aspects of the invention that HBr be used as the start-up reflux fluid, it is not intended that the invention be limited by this preference. In certain aspects of the invention, it is preferred that the start-up reflux fluid have a boiling temperature of from about 100° C. to about 126° C. It is also preferred that the start-up reflux fluid be water or an aqueous solution. It is expected that an inventive separation may be continuously run for a significant length of time after introduction of the feed fluid into the column is begun and, therefore, the start-up reflux fluid comprises a relatively insignificant portion of process materials.

Once the column 10 has been prepared as described, a fluid comprising an alkanol and aqueous HBr is metered into the column 10 at a point sufficiently above the vessel 20 to allow the alkanol to be carried upwards, while the acid and most of the water condense and are collected in the vessel along with any non-volatiles present in the feed.

The alkanol, optionally some water, alkyl bromides that were already present in the feed solution and any small amount of alkyl bromide which might be formed during the distillation are carried overhead, condensed and collected. Alkanols, alkyl bromides and water may then be readily separated using processes known in the art. In certain aspects of the invention, alkyl bromides are removed from the fluid feed, such as, for example, TBBPA mother liquor, before it is introduced into the column so that an inventive system can be more readily monitored to determine how much, if any, alkyl bromide is being generated in the distillation system. Where TBBPA mother liquor is being separated, the non-volatiles typically comprise brominated organic molten liquids under these conditions, and will form a separate phase in the reboiler. Conveniently, the acid phase and the organic phase may be continuously drained or pumped from the vessel 20 to permit the distillation to be run in a continuous fashion.

It is understood that the HBr concentrations in the column decrease toward the top of the column and that alkanol concentrations increase toward the top of the column. In a preferred aspect of the invention, the formation of alkyl bromides during distillation is minimized by adjusting process parameters, such as, for example, temperatures, column design, reflux ratios and pressure, to ensure that a quantity of water vapor is carried upwards with the alkanol vapor through zones of the column where acid vapors are still present. The presence of water advantageously prevents the alkanol and the HBr from reacting to form the corresponding alkyl bromide. It is therefore preferred that some water be collected with the alkanol because water is readily separable from the alkanol using processes known in the art. Furthermore, it has been found that carrying over as little as 3 parts water per 100 parts alkanol, by weight, significantly reduces alkyl bromide formation.

It is preferred that the distillate (i.e., the fluid recovered from the condenser 50) comprise at least about 50% of the alkanol originally introduced into the column in the feed fluid, more preferably at least about 80% and, most preferably, at least about 90%. It is also preferred that the weight ratio of alkanol to HBr in the distillate be from about 95:5 to about 100:0.

With respect to the fluid recovered from the vessel 20, it is preferred that this fluid comprise at least about 50% of the HBr originally introduced into the column in the feed fluid, more preferably at least about 80% and, most preferably, at least about 90%. It is also preferred that the weight ratio of alkanol to HBr in this fluid be from about 0:100 to about 5:95, and that this fluid comprise less than about 10% of the alkyl bromide originally introduced into the column in the feed fluid.

Inventive processes advantageously achieve separation of an alkanol and aqueous HBr in a fluid without generating a significant amount of alkyl bromide. The invention will be further described with reference to the following specific Examples. It will be understood that these Examples are illustrative and not restrictive in nature.

EXAMPLE ONE

CONTINUOUS SEPARATION OF AN ALKANOL AND AQUEOUS HYDROBROMIC ACID

A distillation apparatus is provided, as illustrated in FIG. 2, which consists of a 500 ml three neck round bottom flask 25 with bottom drain 26, thermometer 27, and an electric heating mantle 28. One neck 29 is fitted with a lower 28 mm diameter 10 tray Oldershaw distillation column 12 and a similar upper 5 tray column 18, the columns being connected with a Claisen adapter 16 having a side arm 17. Both columns 12, 18 are mirrored and vacuum jacketed. The top 19 of the upper column 18 is capped with a magnetically controlled distillation head (not shown) which is used to govern the reflux ratio. Connected to the distillation head are a condenser 55 maintained between about 0 and about minus 6° C. and a receiver (or "receptacle") comprising a 500 ml flask 45 immersed in a dry ice bath 46 to prevent loss of alkyl bromide. The side arm 17 is used as the feed port for introduction of the fluid to be separated. Metering of the fluid is accomplished with a Masterflex pump 60. Tubing from a second Masterflex pump 65 is inserted through the second neck 24 of reboiler 25. This is used to pump the aqueous HBr bottoms product from the reboiler in order to maintain a relatively constant level. The lower phase of molten organics can be either pumped out through another dip tube or periodically drained through the bottom drain valve 26.

At the start of the procedure, the reboiler is charged with about 50 to about 70 grams of aqueous HBr. Heat is then applied to the reboiler until vapors reach the top 19 of the column. Introduction of a fluid feed comprising an alkanol and aqueous hydrobromic acid is then begun through the Claisen side arm 17. Feed rate is maintained at a rate which prevents the flow of alkanol to the reboiler while maintaining the reboiler at a temperature of from about 100° C. to about 126° C. when the distillation is conducted at atmospheric pressure. After about an 8 hour run time, the feed is stopped, distillate and bottoms are collected and analyzed for the amounts of alkanol, alkyl bromide, water and HBr. At least about 50% of the alkanol is in the distillate and at least about 50% of the HBr is in the bottoms product. Little or no alkyl bromide is formed.

EXAMPLE TWO

SEPARATION OF TBBPA MOTHER LIQUOR TO YIELD A DRY DISTILLATE

At the start of the procedure, using the equipment of Example 1, the reboiler was charged with 58 grams of 28% aqueous HBr. Heat was applied to the reboiler and at a pot temperature of about 113° C., vapors reached the top of the column. Feed of TBBPA mother liquor containing 50.8% methanol, 5.2% methyl bromide, 29.0% water and 18.5% HBr by weight was begun through the Claisen side arm. It is important to note with respect to this and the other Examples that weights of solution components provided were determined by analysis and may not always account for 100% of the materials charged. Also, all distillations were carried out at atmospheric pressure; however, inventive processes may be conducted at pressures above or below atmospheric pressure and it is well within the purview of a person skilled in the art to make appropriate adjustments.

Feed rate was maintained at approximately 2.2 grams per minute while holding a pot temperature of 107–111° C. and a head temperature of 62–63° C. After about 8 hours, the feed was stopped and the distillate and bottoms product were analyzed. The results are shown in Table 1.

TABLE 1

RESULTS OF CONTINUOUS DISTILLATION WITH COLUMN FEED (OBJECTIVE OF DRY METHANOL)

|  | | Amount of Component by Analysis, grams | | |
|---|---|---|---|---|---|
|  | Actual Wt., g | Methanol | Methyl Br | Water | HBr |
| M/L Feed | 1036.8 | 527.0 | 54.2 | 301.0 | 191.5 |
| Charged to Pot | 58.4 | 0.00 | 0.0 | 41.8 | 16.6 |
| Overheads | 527.7 | 466.0 | 76.1 | 4.8 | 0.8 |
| Bottoms | 538.7 | 12.1 | 0.7 | 347.6 | 171.9 |

These results show that a very large portion of the methanol was successfully recovered, and that the distillate contained less than 1% of water. The trade-off was that a quantity of methyl bromide was generated during the process. However, that only represents a 42% increase over the amount already present in the mother liquor feed.

EXAMPLE THREE (COMPARATIVE)

POT DISTILLATION WITHOUT COLUMN FEED

Figure 3:
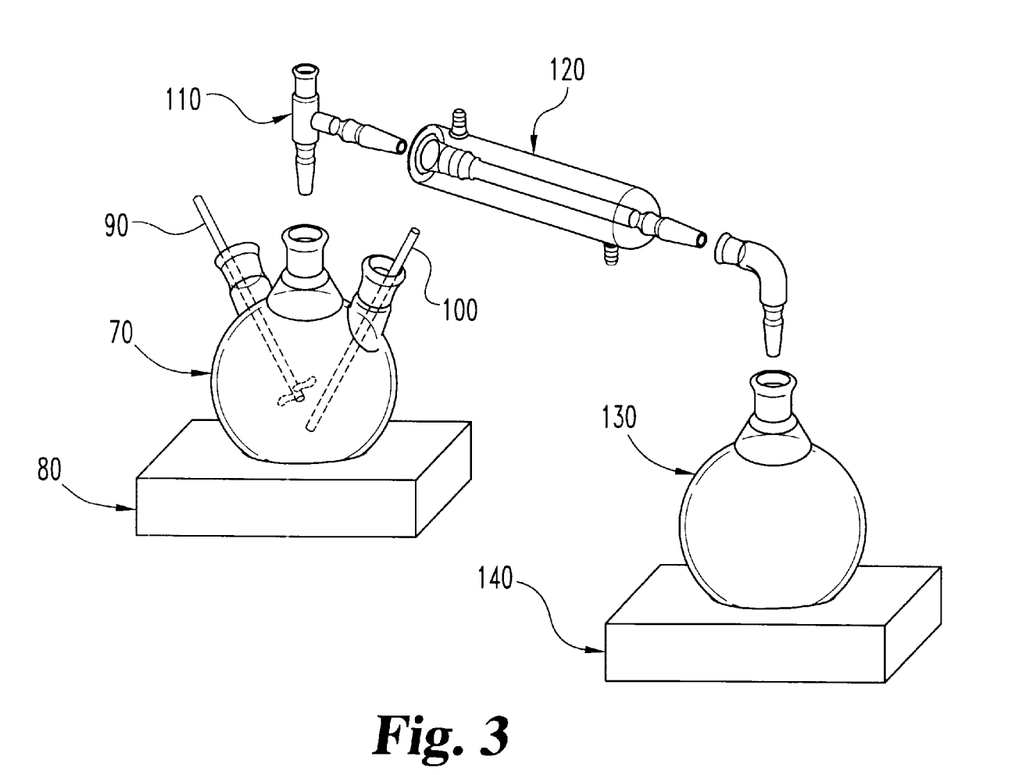
FIG. 3 illustrates a simple distillation system as used in Comparative Example Three.

As depicted in FIG. 3, a three neck 1000 ml round bottom flask 70 was fitted with an electrical heating mantle 80, mechanical stirrer 90, thermometer 100, and a distillation head 110 connected to a condenser 120 maintained between 0 and minus 6° C. Condensed liquids were collected in a 500 ml flask 130 immersed in a dry ice bath 140 to prevent loss of methyl bromide. The distillation flask 70 was charged with 935.1 grams of mother liquor generated from a preparation of tetrabromobisphenol-A. The mother liquor as received contained 48.5% methanol, 2.4% methyl bromide, 30.2% water, and 18.1% HBr by weight. It also contained minor amounts of brominated phenols and elemental bromine. Heat and stirring were applied to the distillation flask 70 and about 70% of the liquid was carried overhead as a vapor and condensed. During the process the pot temperature ranged from 60–105° C. while the head temperature climbed from 44 to 100° C.

Heat was removed from the distillation flask and the quantities of bottoms and distillate were measured and then analyzed with the results shown in Table 2. Note that the true weights of the streams are presented in the second column, but that the weights of the components are based on analysis of those streams. The sum of the component weights does not exactly match the stream weight because of the difficulty in measuring concentrations of these mixtures.

TABLE 2

RESULTS OF BATCH DISTILLATION WITHOUT COLUMN FEED

|  | | Amount of Component by Analysis, grams | | |
|---|---|---|---|---|---|
|  | Actual Wt., g | Methanol | Methyl Br | Water | HBr |
| Charged to Pot | 935.1 | 453.5 | 22.3 | 282.4 | 169.3 |
| Overheads | 668.5 | 437.5 | 97.4 | 145.1 | 1.7 |
| Bottoms | 251.7 | 2.5 | 1.2 | 158.8 | 86.6 |

These results show that it is possible to recover most of the valuable components from TBBPA mother liquor by using simple distillation. Much of the methanol was carried overhead and collected with only a small amount of acid being included. But even though a large amount of water was also co-distilled, it did not prevent the formation of a large amount of methyl bromide. Starting with only 22.3 grams of methyl bromide in the original mother liquor, a manufacturer would now have to contend with 98.6 grams of it after distillation. That represents a 342% increase over the starting amount.

EXAMPLE FOUR

CONTINUOUS DISTILLATION OF TBBPA MOTHER LIQUOR WITH COLUMN FEED TO PRODUCE A WET DISTILLATE TO MINIMIZE FORMATION OF METHYL BROMIDE

Using the equipment of Example 1, conditions were adjusted to provide for a more concentrated acid solution in the reboiler and a higher head temperature. This resulted in co-distillation of a portion of the water with the methanol and methyl bromide, but inhibited additional methyl bromide formation.

At the start of the procedure, the reboiler was charged with 59.2 grams of 48% aqueous HBr. Heat was applied to the reboiler and at a pot temperature of about 120° C., vapors reached the top of the column. Feed of TBBPA mother liquor containing 45.2% methanol, 5.2% methyl bromide, 27.4% water and 22.4% HBr by weight was begun through the Claisen side arm. Feed rate was maintained at approximately 2.9 grams per minute while holding a pot temperature of 118–120° C. and a head temperature of 64–67° C. The pot temperature indicated that the acid concentration was probably being maintained at about 45% HBr. After about 7 hours, the feed was stopped, distillate and bottoms collected and analyzed. The results are shown in Table 3.

TABLE 3

RESULTS OF CONTINUOUS DISTILLATION WITH COLUMN FEED
(OBJECTIVE OF MINIMIZED METHYL BROMIDE)

| | Actual Wt., g | Amount of Component by Analysis, grams | | | |
|---|---|---|---|---|---|
| | | Methanol | Methyl Br | Water | HBr |
| M/L Feed | 1240.3 | 561.0 | 64.3 | 340.2 | 278.1 |
| Charged to Pot | 59.2 | 0.0 | 0.0 | 30.8 | 28.4 |
| Overheads | 650.1 | 548.6 | 55.0 | 17.9 | 6.5 |
| Bottoms | 630.4 | 6.9 | 0.9 | 333.8 | 278.6 |

These results show that almost all methanol can be recovered from the mother liquor using these run conditions. Using this preliminary design the distillate did contain about 3% water and 1% acid, but optimization would be expected to lower these values. Most importantly, within the limits of analyzing these complex streams, there was no methyl bromide formed during the distillation.

EXAMPLE FIVE

CONTINUOUS DISTILLATION WITH COLUMN FEED OF TBBPA MOTHER LIQUOR PREPARED USING ETHANOL

Using the equipment of Example 1, the reboiler is charged with aqueous HBr. Heat is applied to the reboiler until vapors reach the top of the column. Feed of TBBPA mother liquor containing ethanol, ethyl bromide, water and HBr is begun through the Claisen side arm. Feed rate is maintained at a rate which prevents the flow of ethanol to the reboiler while maintaining the reboiler at a temperature of from about 100° C. to about 126° C. when the distillation is conducted at atmospheric pressure. After about 7–8 hours, the feed is stopped, and distillate and bottoms are collected and analyzed. At least about 50% of the alkanol is in the distillate and at least about 50% of the HBr is in the bottoms product. Little or no alkyl bromide is formed.

EXAMPLE SIX

CONTINUOUS DISTILLATION WITH COLUMN FEED OF TBBPA MOTHER LIQUOR PREPARED USING 1-PROPANOL

Using the equipment of Example 1, the reboiler is charged with aqueous HBr. Heat is applied to the reboiler until vapors reach the top of the column. Feed of TBBPA mother liquor containing 1-propanol, 1-propyl bromide, water and HBr is begun through the Claisen side arm. Feed rate is maintained at a rate which prevents the flow of 1-propanol to the reboiler while maintaining the reboiler at a temperature of from about 100° C. to about 126° C. when the distillation is conducted at atmospheric pressure. After about 7–8 hours, the feed is stopped, and distillate and bottoms are collected and analyzed. At least about 50% of the alkanol is in the distillate and at least about 50% of the HBr is in the bottoms product. Little or no alkyl bromide is formed.

What is claimed is:

1. A process for separating an alkanol from aqueous hydrobromic acid, comprising:

providing a reflux environment of aqueous hydrobromic acid in a fractionating column having a bottom end, a top end, and a port located between the top and bottom ends and in fluid communication with the column;

feeding into the column through the port a first fluid comprising an alkanol and aqueous hydrobromic acid;

recovering from the top end a second fluid comprising at least about 50% of the alkanol; and recovering from the bottom end a third fluid comprising at least about 50% of the aqueous hydrobromic acid.

2. The process in accordance with claim 1, wherein the second fluid comprises at least about 80% of the alkanol; and wherein the third fluid comprises at least about 80% of the aqueous hydrobromic acid.

3. The process in accordance with claim 1, wherein the column has a predetermined length and wherein the port is positioned a distance of at least one tenth of the length from the bottom of the column.

4. The process in accordance with claim 1, wherein the column has a predetermined length and wherein the port is positioned a distance of at least one tenth of the length from the top of the column.

5. A process for separating an alkanol from aqueous hydrobromic acid, comprising:

providing a distillation system comprising a distillation column having a bottom end, a top end and a port located between the top and bottom ends for introducing a fluid into the column; first means adjacent the bottom end and in fluid communication with the column for receiving a bottoms product from the column; and second means adjacent the top end and in fluid communication with the column for receiving a distillate; wherein a fourth fluid is contained in the first means; and wherein the fourth fluid is a liquid;

boiling the fourth fluid to provide a reflux environment in the column;

feeding into the column through the port a first fluid comprising an alkanol and aqueous hydrobromic acid;

recovering from the second means a second fluid comprising at least about 50% of the alkanol; and recovering from the first means a third fluid comprising at least about 50% of the aqueous hydrobromic acid.

6. The process in accordance with claim 5, wherein the second fluid comprises at least about 80% of the alkanol; and wherein the third fluid comprises at least about 80% of the aqueous hydrobromic acid.

7. A process for separating an alkanol from aqueous hydrobromic acid, comprising:

providing a distillation system comprising a distillation column having a bottom end, a top end and a port located between the top and bottom ends for introducing a fluid into the column; a vessel attached to the column adjacent the bottom end and in fluid communication with the column; and a condenser attached to the column adjacent the top end and in fluid communication with the column; wherein a fourth fluid is contained in the vessel; and wherein the fourth fluid is a liquid;

boiling the fourth fluid to provide a reflux environment in the column;

feeding into the column through the port a first fluid comprising an alkanol and aqueous hydrobromic acid;

recovering from the condenser a second fluid comprising at least about 50% of the alkanol; and recovering from the vessel a third fluid comprising at least about 50% of the aqueous hydrobromic acid.

8. The process in accordance with claim 7, wherein the fourth fluid has a boiling point of from about 100° C. to about 126° C.

9. The process in accordance with claim 7, wherein the fourth fluid is selected from the group consisting of water and an aqueous solution.

10. The process in accordance with claim 7, wherein the second fluid comprises at least about 80% of the alkanol; and wherein the third fluid comprises at least about 80% of the aqueous hydrobromic acid.

11. The process in accordance with claim 7, wherein the fourth fluid is aqueous hydrobromic acid.

12. The process in accordance with claim 7, wherein the first fluid further comprises up to about 40% alkyl bromide by weight; and wherein the total amount of alkyl bromide in the second and third fluids is not substantially greater than the amount of alkyl bromide in the first fluid.

13. The process in accordance with claim 7, wherein the first fluid comprises a weight ratio of alkanol to hydrobromic acid of from about 10:90 to about 98:2.

14. The process in accordance with claim 7, wherein the first fluid comprises a weight ratio of alkanol to hydrobromic acid of from about 35:65 to about 85:15.

15. The process in accordance with claim 7, wherein the first fluid comprises a weight ratio of alkanol to hydrobromic acid of from about 65:35 to about 75:25.

16. The process in accordance with claim 7, wherein the second fluid comprises a weight ratio of alkanol to hydrobromic acid of from about 95:5 to about 100:0.

17. The process in accordance with claim 7, wherein the third fluid comprises a weight ratio of alkanol to hydrobromic acid of from about 0:100 to about 5:95.

18. The process in accordance with claim 7, wherein the first fluid further comprises up to about 40% alkyl bromide by weight; and wherein no more than about 10% of the alkyl bromide passes into the third fluid.

19. The process in accordance with claim 7, wherein the first fluid comprises a TBBPA mother liquor.

20. The process in accordance with claim 19, wherein the TBBPA mother liquor further comprises non-volatile materials.

21. The process in accordance with claim 7, wherein the first fluid is a vapor.

22. The process in accordance with claim 7, wherein said feeding comprises:

providing a liquid comprising an alkanol and aqueous hydrobromic acid;

vaporizing the liquid to provide a vapor; and feeding the vapor into the column through the port.

23. The process in accordance with claim 7, wherein the alkanol has a boiling point of less than about 120° C.

24. The process in accordance with claim 7, wherein the alkanol comprises from about 1 to about 4 carbon atoms.

25. The process in accordance with claim 7, wherein the alkanol is selected from the group consisting of methanol, ethanol, n-propanol, isopropanol, isomers of butanol, pentanol and mixtures thereof.

26. The process in accordance with claim 7, wherein the first fluid comprises at least about 5% alkanol by weight.

27. The process in accordance with claim 7, wherein the first fluid comprises from about 40% to about 60% alkanol by weight.

28. The process in accordance with claim 7, wherein the first fluid comprises from about 15% to about 30% hydrobromic acid by weight.

29. The process in accordance with claim 7, wherein the aqueous hydrobromic acid comprises less than about 48% hydrobromic acid by weight.

30. The process in accordance with claim 29, wherein the aqueous hydrobromic acid comprises from about 20% to about 45% hydrobromic acid by weight.

* * * * *